June 17, 1952 E. S. BOERNER Plant Pat. 1,106
CHRYSANTHEMUM PLANT
Filed May 25, 1951
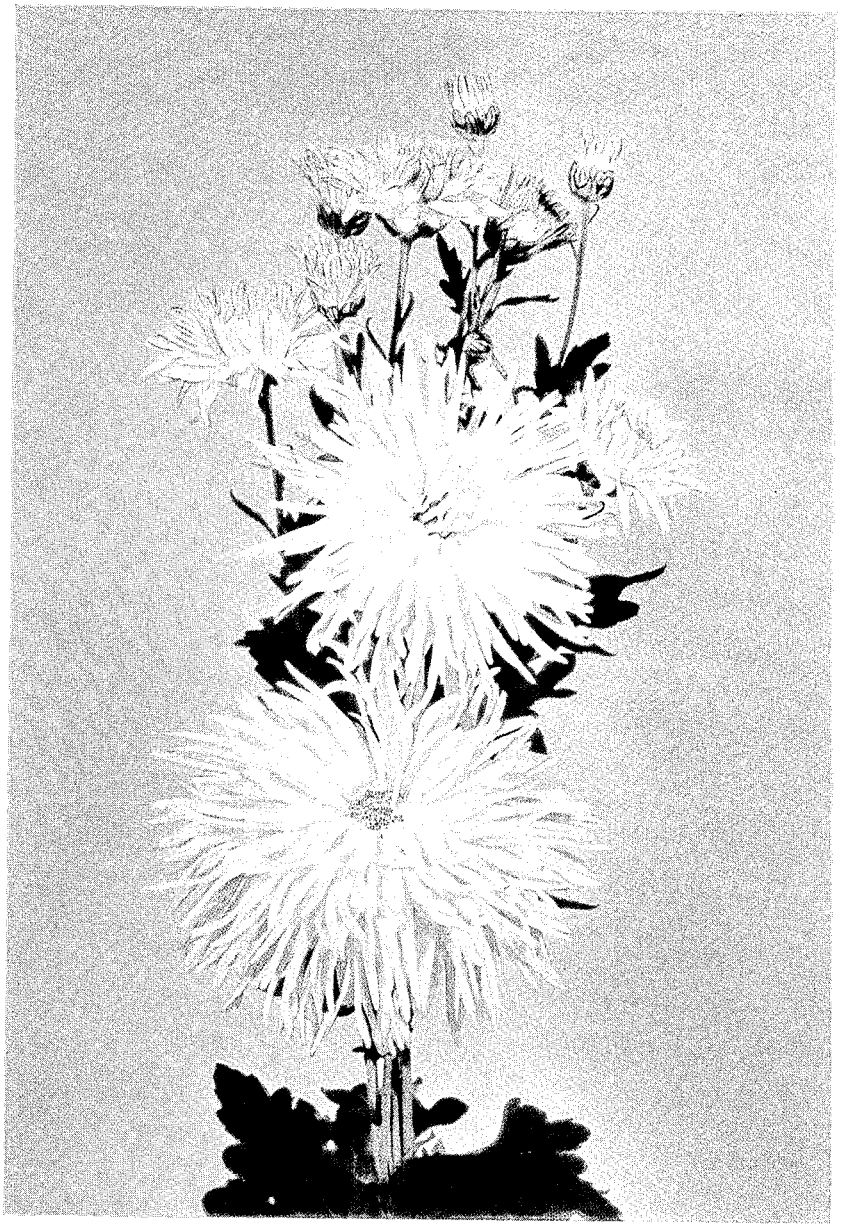
Inventor.
E. S. Boerner
By: Robb & Robb
Attorneys.

Patented June 17, 1952

Plant Pat. 1,106

UNITED STATES PATENT OFFICE 1,106

CHRYSANTHEMUM PLANT

Eugene S. Boerner, Newark, N. Y., assignor to Jackson & Perkins Company, Newark, N. Y., a corporation of New York Application May 25, 1951, Serial No. 223,240

1 Claim. (Cl. 47—60)

The present invention relates to a new and distinct variety of chrysanthemum plant, originated by me by crossing the yellow variety known as "Avalanche" (unpatented) with an unnamed and unpatented seedling of "Lavender Lady" (unpatented) × "Pale Moon" (unpatented).

The primary objective in making this cross was to obtain a larger, earlier and hardier outdoor chrysanthemum. Accordingly, the variety yellow "Avalanche" was used as the male parent and the seedling of "Lavender Lady" × "Pale Moon" was used as the pollen parent, and this cross fully achieved the desired objective, as evidenced by the following dominant and unique combination of characteristics which definitely distinguish this new variety from its parents, as well as from all other known varieties:

(1) Large decorative type of flowers of Pale Flesh color overcast with Maize Yellow in general tonality;

(2) Shaggy effect of the flowers resulting from the twisting of each of the long, thin petals, thereby producing an appearance that is entirely different from any hardy chrysanthemum variety heretofore known;

(3) Long-lasting quality of the flowers;

(4) Freedom of bloom.

Asexual reproduction of the new variety by top cuttings and also by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed at Newark, New York, with color terminology in accordance with Ridgway's Color Standards and Nomenclature:

Parentage:
- *Male parent.*—Yellow "Avalanche."
- *Pollen parent.*—An unnamed seedling of "Lavender Lady" × "Pale Moon."

Classification: Decorative type.

Growth: Upright; clean; attaining height of 24 inches.

Cold resistance: Plants are hardy and do not burn and are not injured by frost.

Blooming period: In Newark, New York, climatic area, date of start of bloom August 30, and the plant makes a big show until severe freezing in October and November.

Bud:
- *Color.*—When sepals first divide—Sea-Foam Yellow, Plate 31. When petals begin to unfurl—White, Plate 53, lightly overcast with Flesh Color, Plate 14. When half blown—inside of petals—Maize Yellow, Plate 4, lightly overcast with Pale Flesh Color, Plate 14. Reverse of petals—White, Plate 53, overcast with Maize Yellow, Plate 4.
- *Peduncle.*—Color—Light Cress Green, Plate 31. Strength—stiff; slender.

Bloom:
- *Size.*—4 to 4½ inches.
- *Stems.*—Strong; normal.
- *Form.*—Decorative type.
- *Petalage.*—Very double; when flower is fully open, center pistils fully exposed.
- *Color.*—Center of flower—Pale Flesh Color, Plate 14, overcast with Maize Yellow, Plate 4. Outer petals—Marguerite Yellow, Plate 30, slightly overcast with Pale Salmon Color, Plate 14. Base of petals—Marguerite Yellow, Plate 30. Inside of petals—Marguerite Yellow, Plate 30, overcast with Pale Flesh Color, Plate 14. Reverse of petals—Marguerite Yellow, Plate 30, overcast lightly with Seashell Pink, Plate 14. General tonality—Pale Flesh Color, Plate 14, overcast with Maize Yellow, Plate 4.

Petals:
- *Texture.*—Thick.
- *Form.*—Long; narrow; wavy towards end of petal.

Fragrance: Slight; lemon.

Plant:
- *Form.*—Upright.
- *Growth.*—Vigorous and free.

Foliage:
- *Size.*—Large.
- *Quantity.*—Normal.
- *Color.*—Upper side—Cress Green, Plate 31. Reverse side—Chromium Green, Plate 32.
- *Texture.*—Leathery.

I claim:

A new and distinct variety of chrysanthemum plant of the decorative type, characterized as to novelty by its hardiness, by its large decorative type flowers of Pale Flesh color overcast with Maize Yellow in general tonality, by the shaggy effect of the flowers resulting from the twisting of each of the long, thin petals, by the long-lasting quality of its flowers, and by its freedom of bloom, substantially as herein shown and described.

EUGENE S. BOERNER.

No references cited.